United States Patent
Abdulla (10) Patent No.: US 12,020,825 B2
(45) Date of Patent: Jun. 25, 2024

(54) COMPUTER SYSTEM AND METHOD FOR DETERMINING EFFICACY OF A MEDICAL TREATMENT FOR A MEDICAL CONDITION

(71) Applicant: DIGIPHARM LTD, Swansea (GB)

(72) Inventor: Ahmed Abdulla, Therwil (CH)

(73) Assignee: DIGIPHARM LTD, Swansea (GB)

( * ) Notice: Subject to any disclaimer, the term of this patent is extended or adjusted under 35 U.S.C. 154(b) by 605 days.

(21) Appl. No.: 17/281,887

(22) PCT Filed: Oct. 1, 2019

(86) PCT No.: PCT/EP2019/076597
§ 371 (c)(1),
(2) Date: Mar. 31, 2021

(87) PCT Pub. No.: WO2020/070130
PCT Pub. Date: Apr. 9, 2020

(65) Prior Publication Data
US 2021/0398687 A1 Dec. 23, 2021

(30) Foreign Application Priority Data

Oct. 1, 2018 (CH) .................................. 01194/18
Nov. 16, 2018 (CH) .................................. 01426/18

(51) Int. Cl.
*G16H 50/70* (2018.01)
*G06F 16/23* (2019.01)
(Continued)

(52) U.S. Cl.
CPC ......... *G16H 50/70* (2018.01); *G06F 16/2315* (2019.01); *G16H 10/60* (2018.01);
(Continued)

(58) Field of Classification Search
CPC ........ G16H 50/70; G16H 40/20; G16H 10/60; G16H 50/30; G16H 20/10; G06F 16/2315
See application file for complete search history.

(56) References Cited

U.S. PATENT DOCUMENTS

| 9,665,685 B1 * | 5/2017 | Paris, III | G16H 15/00 |
| 2010/0191071 A1 * | 7/2010 | Anderson | G16H 50/50 |
| | | | 703/11 |

(Continued)

FOREIGN PATENT DOCUMENTS

| WO | WO 2018/039312 A1 | 3/2018 | |
| WO | WO-2019074191 A1 * | 4/2019 | A61N 5/103 |

OTHER PUBLICATIONS

Azaria, Asaph. MedRec: Using Blockchain for Medical Data Access and Permission Management. 2016 2nd International Conference on Open and Big Data. (Year: 2016).*

(Continued)

*Primary Examiner* — Jason S Tiedeman
*Assistant Examiner* — Tristan Isaac Evans
(74) *Attorney, Agent, or Firm* — Knobbe Martens Olson & Bear LLP (57) ABSTRACT

Users indicate possible outcomes of a medical treatment of a medical condition, a population of patients (4) to be treated, and data sources (3) for providing related health data. A smart contract (81) on a blockchain (8) comprises code (82) and an assessment data structure (83). The assessment data structure (83) defines data related to the treatment and to be collected from the data sources (3) and an assessment block (84) to be generated and stored on the blockchain (8), using the data collected during an assessment period. The assessment block (84) indicates for the assessment period the outcomes actually achieved by the treatment. The smart contract code (82) controls processors (11) to determine the efficacy of the treatment, upon an (Continued)

assessment block (84) being stored on the blockchain (8), using the outcomes indicated in the assessment block (84).

15 Claims, 3 Drawing Sheets

(51) Int. Cl.
  *G16H 10/60* (2018.01)
  *G16H 40/20* (2018.01)
  *G16H 20/10* (2018.01)
  *G16H 50/30* (2018.01)
(52) U.S. Cl.
  CPC ............. *G16H 40/20* (2018.01); *G16H 20/10* (2018.01); *G16H 50/30* (2018.01)

(56) References Cited

U.S. PATENT DOCUMENTS

| | | | |
|---|---|---|---|
| 2017/0161439 A1* | 6/2017 | Raduchel | G16H 10/60 |
| 2017/0344580 A1* | 11/2017 | King | H04L 9/3247 |
| 2018/0165588 A1 | 6/2018 | Saxena et al. | |
| 2018/0350451 A1* | 12/2018 | Ohnemus | G16H 40/67 |
| 2019/0378597 A1* | 12/2019 | Ramakrishnan | G16H 20/10 |

OTHER PUBLICATIONS

Suk. Machine Translation of WO 2019/074191 A1. (Year: 2019).*
Timothy Nugent. Improving data transparency in clinical trial using blockchain smart contracts. F1000 Research. Oct. 20, 2016. (Year: 2016).*
Raman. On the Information Theory of Clustering, Registration, and Blockchains. Doctor of Philosophy in Electrical and Computer Engineering in the Graduate College of the University of Illinois at Urbana-Champaign, 2019. (Year: 2019).*
Azaria. MedRec: Using Blockchain for Medical Data Access and Permission Management. 2016 2nd International Conference on Open and Big Data. (Year: 2016).*
WO-2019074191-A1 machine translation (Year: 2019).*
International Search Report and Written Opinion of the International Searching Authority for Internatinoal Application No. PCT/EP2019/076597, dated Dec. 13, 2019, in 22 pages.
Abdulla, "Supply chain and beyond: Blockchain in healthcare," Hangzhou Forum: Blockchain in Trade Facilitation: Looking Toward Implementation, XP055569244 (Oct. 15, 2018), Hangzhou Forum of United Nations Centre for Trade Facilitation and Electronic Business (UN/CEFACT) (Oct. 14-19, 2018).
Azaria et al., "MedRec: Using Blockchain for Medical Data Access and Permission Management," 2016 2nd International Conference on Open and Big Data (OBD), IEEE, pp. 25-30, XP032969608 (Aug. 22, 2016).
Anonymous, "Digipharm Whitepaper (EN) V.2.0", XP055569039 (Jun. 1, 2018). Retrieved from the Internet: URL: https://digipharm.io/docs/Digipharm_Whitepaper_EN_v2.0.pdf [retrieved on Mar. 14, 2019].
Anonymous, "Digipharm—Whitepaper (EN) v.2.2", XP055569019 (Oct. 1, 2018). Retrieved from the Internet: URL: https://digipharm.io/docs/Digipharm_Whitepaper_EN_v2.2.pdf [retrieved on Mar. 14, 2019].
Anonymous, "Introducing Digipharm: Bringing Value Based Healthcare to Life Using Blockchain Technology", XP055569060 (Feb. 20, 2018). Retrieved from the Internet: URL: https://medium.com/digipharm/introducing-digipharm-bringing-value-based-healthcare-to-life-using-blockchain-technology-d560782d43c1 [retrieved on Mar. 14, 2019].
Anonymous: "Digipharm—WhitePaper Review", Youtube, XP054979209 (Apr. 1, 2018). Retrieved from the Internet: URL: https://www.youtube.com/watch?v=gsISIGaHjDk [Link to Video Only].
Benchoufi et al., "Blockchain technology for improving clinical research quality," Trials, vol. 18(1), XP055569855, GB ISSN: 1745-6215 (Dec. 19, 2017).
Genovese et al., "Longterm Safety and Efficacy of Subcutaneous Abatacept in Patients with Rheumatoid Arthritis: 5-year Results from a Phase IIIb Trial," Journal of Rheumatology, vol. 45(8), pp. 1085-1092, XP055645758, CA ISSN: 0315-162X (Apr. 15, 2018).
Kleinaki et al., "A Blockchain-Based Notarization Service for Biomedical Knowledge Retrieval," Computational and Structural Biotechnology Journal, vol. 16, pp. 288-297, XP055569868 Sweden (Aug. 17, 2018).
Nugent et al., "Improving data transparency in clinical trials using blockchain smart contracts," FI000Research, vol. 5, p. 2541, XP055569539 (Oct. 20, 2016).
Rakic, "Blockchain Technology in Healthcare," Proceedings of the 4th International Conference on Information and Communication Technologies for Ageing Well and e-Health, pp. 13-20, XP055569568 (Mar. 23, 2018).
Siyal et al., "Applications of Blockchain Technology in Medicine and Healthcare: Challenges and Future Perspectives," cryptography, vol. 3(1), p. 3, XP055569222 (Jan. 2, 2019).
Zhang et al., "FHIRChain: Applying Blockchain to Securely and Scalably Share ClinicalData," Computational and Structural Biotechnology Journal, vol. 16, pp. 267-278, XP055569605 Sweden (Jul. 29, 2018).

* cited by examiner

COMPUTER SYSTEM AND METHOD FOR DETERMINING EFFICACY OF A MEDICAL TREATMENT FOR A MEDICAL CONDITION

FIELD OF THE INVENTION

The present invention relates to a computer system and a method for determining efficacy of a medical treatment for a medical condition. Specifically, the present invention relates to a computer system comprising one or more processors and a computer-implemented method of determining the efficacy of a medical treatment for a medical condition.

BACKGROUND OF THE INVENTION

It has been argued that digitalization of healthcare is a key element for an efficient health care system which improves patient outcomes, their quality of life and reduces the huge cost on health systems worldwide. The healthcare industry is experiencing a paradigm shift to value-based care due to growth in demand, aging populations, chronic diseases and unsustainable levels of health-related expenditure. Health systems are transitioning toward value-based care to prevent the rationing of services and increased costs for patients and payers without compromising quality of care. Provision of healthcare from a value-based perspective is based on the underlying aim of generating optimal patient outcomes relative to the monetary spend. Healthcare systems are advancing from 'fee-for-service' reimbursement models to 'fee for performance' models that are linked to patient outcomes. By 2020, it is estimated that 75% of commercial payments for healthcare will be executed according to value-based agreements (Deloitte). There are early signs of this paradigm shift on a global scale as some healthcare stakeholders are re-aligning their practices in anticipation of this shift. Value-based pricing schemes offer an increasingly dynamic solution to current healthcare problems, where risk and uncertainty is shared between healthcare systems and manufacturers, and the level of reimbursement is linked to the overall value provided. Value-based pricing schemes conform to a 'fee for performance' reimbursement model linked to patient outcomes rather than pricing based on volume or units of drug consumed as a 'fee for service'. Beyond drug therapy, this approach to commissioning is applicable to health technology such as medical devices, wider healthcare provision and social care. Value-based pricing agreements are one of a range of options within a suite of innovative pricing solutions. Ultimately, these solutions are set-up with the aim of providing access to the right healthcare, at the right time for patients and at the right cost for the healthcare system and manufacturers. However, difficulties in tracking patient outcomes, the administrative burden of processing pricing agreements, fragmented health systems and data accessibility act as major barriers to the desired restructuring of health care systems. What is needed is a system for determining efficiently and accurately the efficacy of a particular medical treatment for a particular medical condition. More specifically, there is a need for determining efficiently and accurately the efficacy of a particular medical drug or device used in the treatment of a particular medical condition.

SUMMARY OF THE INVENTION

It is an object of this invention to provide a computer system and a method for determining the efficacy of a medical treatment for a medical condition. In particular, it is an object of the present invention to provide a computer system and a method for determining the efficacy of a medical treatment for a medical condition, e.g. using a particular drug and/or medical device, which computer system and method do not have at least some of the disadvantages of the prior art.

According to the present invention, these objects are achieved through the features of the independent claims. In addition, further advantageous embodiments follow from the dependent claims and the description.

According to the present invention, the above-mentioned objects are particularly achieved in that a computer system for determining efficacy of a medical treatment for a medical condition comprises one or more processors which are configured to perform the steps of: receiving from one or more users, prior to performing the medical treatment of the medical condition, indications of a plurality of possible outcomes expected from the medical treatment of the medical condition, identification of a population of patients to be treated, identification of one or more data sources for providing health care data related to the medical treatment of the population for the medical condition, and a definition of an assessment periodicity; generating and storing on an assessment blockchain, related to collecting and processing health care data for determining the efficacy of the medical treatment for the medical condition, an assessment smart contract, the assessment smart contract comprising smart contract code and an assessment data structure, the assessment data structure defining for a data collection system data records and data elements which relate to the medical treatment of the population for the medical condition and are to be collected from the data sources with the defined assessment periodicity, and an assessment block to be generated and stored on the assessment blockchain by the data collection system for an assessment period, as defined by the assessment periodicity, using the data records and data elements collected during the assessment period, the assessment block indicating for the assessment period the outcomes actually achieved for the population by the medical treatment of the medical condition, and the smart contract code being configured to control the one or more processors, such that the processors determine the efficacy of the medical treatment for the medical condition for a particular assessment period, upon an assessment block being stored by the data collection system on the assessment blockchain for the particular assessment period, using the outcomes indicated in the assessment block for the population by the medical treatment of the medical condition.

In an embodiment, the processors are further configured to receive from the one or more users a rating level for each of the expected outcomes; and to generate smart contract code configured to control the one or more processors, such that the processors determine the efficacy of the medical treatment by rating the outcomes indicated in the assessment block, using the rating levels indicated for the expected outcomes, upon an assessment block being stored on the assessment blockchain for the particular assessment period.

In an embodiment, the processors are further configured to receive from the one or more users an aggregation level for the population of patients, the aggregation level including at least one of: age, sex, geographic region, and body mass index; and to generate the assessment data structure to further define for the data collection system the aggregation level at which the data records and data elements are to be collected from the data sources, and at which the assessment block is to indicate the outcomes actually achieved by the medical treatment of the medical condition.

In an embodiment, the processors are further configured to receive from the one or more users an indication of at least one of: a medical device and a medical drug, to be used in the medical treatment of the medical condition; to generate the assessment data structure configured to define for the data collection system data records and data elements which relate to the use of the medical device or medical drug, respectively, in the treatment of the medical condition, and to define the assessment block to indicate the outcomes actually achieved by the use of the medical device or medical drug, respectively, in the treatment of the medical condition; and to generate smart contract code configured to control the one or more processors, such that the processors determine the efficacy of the medical device or medical drug, respectively, for the treatment of the medical condition, using the outcomes indicated in the assessment block for using the medical device or medical drug, respectively, in treatment of the medical condition.

In an embodiment, the processors are further configured to generate smart contract code configured to control the one or more processors, such that the processors generate a data message, depending on the efficacy, upon an assessment block being stored on the assessment blockchain for the particular assessment period.

In an embodiment, the processors are further configured to receive from the one or more users indications of a provider of the medical treatment and a contract authority; and to generate smart contract code configured to control the one or more processors, such that the processors generate a data transaction, between the contract authority and the provider of the medical treatment, depending on the efficacy, upon an assessment block being stored on the assessment blockchain for the particular assessment period.

In an embodiment, the processors are further configured to use one or more defined coding standards for generating the assessment data structure to define for the data collection system the data records and data elements, and the assessment block.

In an embodiment, the processors are further configured to receive from the one or more users indications of a reference population; to generate temporary blockchains for members of the reference population; and to generate on each of the temporary blockchains a references smart contract related to the respective member of the reference population, the references smart contract comprising smart contract code and a reference data structure, the reference data structure defining data records and data elements which relate to reference data from the respective member of the reference population to be considered in determining the efficacy of the medical treatment for the medical condition, the smart contract code of the references smart contract being configured to control the one or more processors to generate and store on the reference blockchain and/or assessment blockchain a reference block; and the smart contract code of the assessment smart contract being configured to control the one or more processors, such that the processors use the reference block on the reference blockchain or assessment blockchain, respectively, in determining the efficacy of the medical treatment for the medical condition.

In addition to the computer system for determining efficacy of a medical treatment for a medical condition, the present invention also relates to a computer-implemented method for determining efficacy of a medical treatment for a medical condition. The method comprises one or more processors performing the steps of: receiving from one or more users, prior to performing the medical treatment of the medical condition, indications of a plurality of possible outcomes expected from the medical treatment of the medical condition, identification of a population of patients to be treated, identification of one or more data sources for providing health care data related to the medical treatment of the population for the medical condition, and a definition of an assessment periodicity; generating and storing on an assessment blockchain, related to collecting and processing health care data for determining the efficacy of the medical treatment for the medical condition, an assessment smart contract, the assessment smart contract comprising smart contract code and an assessment data structure, the assessment data structure defining for a data collection system data records and data elements which relate to the medical treatment of the population for the medical condition and are to be collected from the data sources with the defined assessment periodicity, and an assessment block to be generated and stored on the assessment blockchain by the data collection system for an assessment period, as defined by the assessment periodicity, using the data records and data elements collected during the assessment period, the assessment block indicating for the assessment period the outcomes actually achieved for the population by the medical treatment of the medical condition, and the smart contract code being configured to control the one or more processors, such that the processors determine the efficacy of the medical treatment for the medical condition for a particular assessment period, upon an assessment block being stored by the data collection system on the assessment blockchain for the particular assessment period, using the outcomes indicated in the assessment block for the population by the medical treatment of the medical condition.

In an embodiment, the method further comprises the processors receiving from the one or more users a rating level for each of the expected outcomes; and generating smart contract code configured to control the one or more processors, such that the processors determine the efficacy of the medical treatment by rating the outcomes indicated in the assessment block, using the rating levels indicated for the expected outcomes, upon an assessment block being stored on the assessment blockchain for the particular assessment period.

In an embodiment, the method further comprises the processors receiving from the one or more users an aggregation level for the population of patients, the aggregation level including at least one of: age, sex, geographic region, and body mass index; and generating the assessment data structure to further define for the data collection system the aggregation level at which the data records and data elements are to be collected from the data sources, and at which the assessment block is to indicate the outcomes actually achieved by the medical treatment of the medical condition.

In an embodiment, the method further comprises the processors receiving from the one or more users an indication of at least one of: a medical device and a medical drug, to be used in the medical treatment of the medical condition; generating the assessment data structure configured to define for the data collection system data records and data elements which relate to the use of the medical device or medical drug, respectively, in the treatment of the medical condition, and to define the assessment block to indicate the outcomes actually achieved by the use of the medical device or medical drug, respectively, in the treatment of the medical condition; and generating smart contract code configured to control the one or more processors, such that the processors determine the efficacy of the medical device or medical drug, respectively, for the treatment of the medical condition, using the outcomes indicated in the assessment block for using the medical device or medical drug, respectively, in treatment of the medical condition.

In an embodiment, the method further comprises the processors generating smart contract code configured to control the one or more processors, such that the processors generate a data message, depending on the efficacy, upon an assessment block being stored on the assessment blockchain for the particular assessment period.

In an embodiment, the method further comprises the processors receiving from the one or more users indications of a provider of the medical treatment and a contract authority; and generating smart contract code configured to control the one or more processors, such that the processors generate a data transaction, between the contract authority and the provider of the medical treatment, depending on the efficacy, upon an assessment block being stored on the assessment blockchain for the particular assessment period.

In an embodiment, the method further comprises the processors using one or more defined coding standards for generating the assessment data structure to define for the data collection system the data records and data elements, and the assessment block.

In an embodiment, the method further comprises the processors receiving from the one or more users indications of a reference population; generating temporary blockchains for members of the reference population; and generating on each of the temporary blockchains a references smart contract related to the respective member of the reference population, the references smart contract comprising smart contract code and a reference data structure, the reference data structure defining data records and data elements which relate to reference data from the respective member of the reference population to be considered in determining the efficacy of the medical treatment for the medical condition, the smart contract code of the references smart contract being configured to control the one or more processors to generate and store on the reference blockchain and/or assessment blockchain a reference block, and the smart contract code of the assessment smart contract being configured to control the one or more processors, such that the processors use the reference block on the reference blockchain or assessment blockchain, respectively, in determining the efficacy of the medical treatment for the medical condition.

In addition to the computer system, the computer-implemented method for determining efficacy of a medical treatment for a medical condition, the present invention also relates to a computer program product comprising a non-transitory computer-readable medium having stored thereon computer program code configured to control one or more processors of a computer system, such that the computer system performs the steps of: receiving from one or more users, prior to performing the medical treatment of the medical condition, indications of a plurality of possible outcomes expected from the medical treatment of the medical condition, identification of a population of patients to be treated, identification of one or more data sources for providing health care data related to the medical treatment of the population for the medical condition, and a definition of an assessment periodicity; generating and storing on an assessment blockchain, related to collecting and processing health care data for determining the efficacy of the medical treatment for the medical condition, an assessment smart contract, the assessment smart contract comprising smart contract code and an assessment data structure, the assessment data structure defining for a data collection system data records and data elements which relate to the medical treatment of the population for the medical condition and are to be collected from the data sources with the defined assessment periodicity, and an assessment block to be generated and stored on the assessment blockchain by the data collection system for an assessment period, as defined by the assessment periodicity, using the data records and data elements collected during the assessment period, the assessment block indicating for the assessment period the outcomes actually achieved for the population by the medical treatment of the medical condition, and the smart contract code being configured to control the one or more processors, such that the processors determine the efficacy of the medical treatment for the medical condition for a particular assessment period, upon an assessment block being stored by the data collection system on the assessment blockchain for the particular assessment period, using the outcomes indicated in the assessment block for the population by the medical treatment of the medical condition.

BRIEF DESCRIPTION OF THE DRAWINGS

The present invention will be explained in more detail, by way of example, with reference to the drawings in which.

DETAILED DESCRIPTION OF THE PREFERRED EMBODIMENTS

Figure 1:
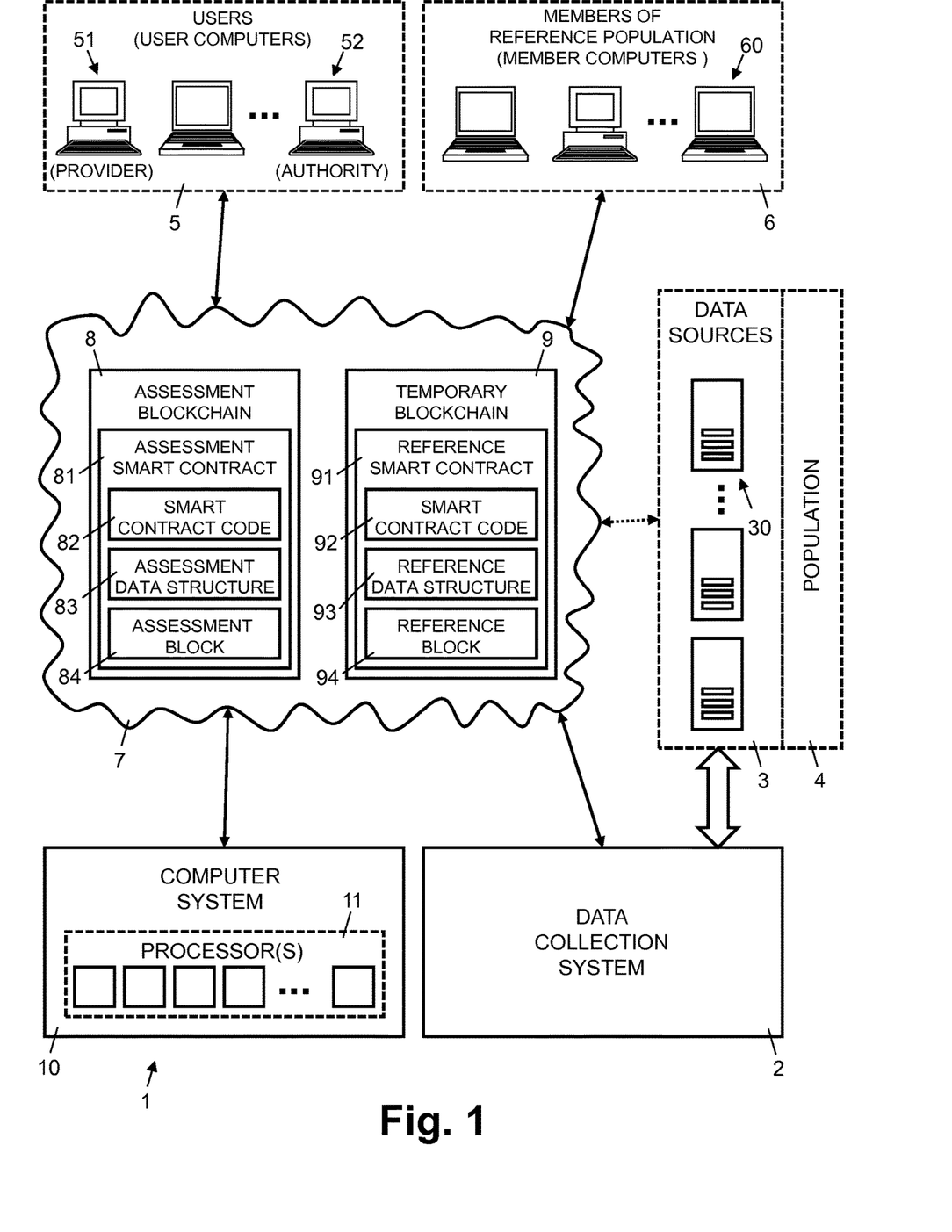
FIG. 1: shows a block diagram illustrating schematically a computer system for determining efficacy of a medical treatment for a medical condition.

In Figure reference numeral 1 refers to a computerized system for determining efficacy of a medical treatment for a medical condition. The computer system 10 comprises one or more computers with one or more processors 11.

Reference numeral 2 refers to a data collection system, specifically a computerized data lake including a secure UID (User Identity) platform 20 for data anonymization. The data collection system 2 comprises one or more computers with one or more processors.

Reference numerals 5 refers to users of the system, specifically to user computers 51, 52. For example, user computer 51 is associated with a provider of medical treatment for a medical condition, e.g. a manufacturer of a drug or a medical device for the treatment of the medical condition. For example, user computer 52 is associated with a contract authority, e.g. the representative of a health care system making use of and paying for the medical treatment on behalf of patients, specifically a population of patients 4 having the respective medical condition to be treated.

Reference numeral 6 refers to members of a reference population or their member computers 60, respectively. The reference population is healthy and does not have the respective medical condition.

Reference numeral 3 refers to data sources associated with health care providers, e.g. doctors, hospitals, laboratories, other medical practitioners and/or health organisations. The data sources comprise one or more computers 30 with one or more processors.

Reference numeral 7 refers to a communication network. The communication network 7 comprises the Internet and various further communication networks for accessing the Internet, e.g. WLAN (Wireless Local Area Networks) and mobile radio networks, such as GSM (Global System for Mobile Communication) or UMTS (Universal Mobile Communication System). The communication network 7 enables data communication between and among the computers and processors of the computerized system 1, specifically the processors and computers of the computer system 10, the user computers 51, 52, the member computers 60, the computers 30 of the data sources 3, and the computers of the data collection system 2 (including the secure UID platform 20).

Reference numeral 8 refers to a blockchain, specifically labelled "assessment blockchain", as it is related to the assessment of collected health care data. Generated and stored on the assessment blockchain 8 are smart contracts 81. The smart contracts 81 comprise smart contract code 82 and an assessment data structure 83. The smart contracts 81 of the assessment blockchain 8 are specifically labelled "assessment smart contract" 81, as they are related to processing the health care data collected in an assessment period for assessing (determining) the efficacy of the medical treatment for the medical condition for the respective assessment period and targeted population of patients 4. The assessment data structure 83 defines for the data collection system 2 the health care data to be collected and the outcomes to be stored in an assessment block 84. The assessment blockchain 8 is also configured to store the assessment blocks 84 submitted by the data collection system 2. The assessment blocks 84 indicates for the assessment period the outcomes actually achieved for the targeted population of patients 4 by the medical treatment of the medical condition.

Reference numeral 9 refers to a temporary blockchain for recording health data from a member of the reference population 6. Generated and stored on the temporary blockchain 9 are smart contracts 91. The smart contracts 91 comprise smart contract code 92 and a reference data structure 93. The smart contracts 91 of the temporary blockchain 9 are specifically labelled "reference smart contract" 91, as they are related to processing the health care data collected in an assessment period from a member of the reference population 6 for establishing reference data to be considered and used in assessing (determining) the efficacy of the medical treatment for the medical condition for the respective assessment period. The reference data structure 93 defines the medical and health data (data records and data elements) which relate to reference data from the respective member of the reference population 6 and are to be collected and reported in a reference block 94. As illustrated schematically in FIG. 1, the temporary blockchain 9 is also configured to store reference blocks 94 generated and submitted by a respective member of the reference population 6, for which the temporary blockchain 9 was generated. In an embodiment, the members of the reference population 6 are provided with a software program, e.g. an app for a mobile or stationary member computer 60 (e.g. a personal computer, a laptop, a mobile phone, a smart watch, or a tablet computer), which enables the respective member computer 60 to receive from its user, i.e. the respective member of the reference population 6, the medical and health care data for the reference data, as defined by the reference data structure 93, and to generate and submit to the temporary blockchain 9 a corresponding reference block 94. Once data collection from the particular member of the reference population 6 is completed and/or the particular member of the reference population 6 no longer desires to participate, the temporary blockchain 9 is deleted.

The blockchains 8, 9 are permissioned blockchains, e.g. implemented on Hyperledger (IBM). Depending on the level of distribution of the blockchains 8, 9, the processors 11 involved in running the smart contract code 82, 92 and storing the blockchains 8, 9 and their smart contracts 82, 92 (including smart contract code 82, 92 and data structures 83, 93) and assessment blocks 84 or reference blocks 94, respectively, are implemented centralized on one or more computers of the computer system 10, distributed on several computers of the computer system 10, and/or also on user computers 5 and/or member computers 6, respectively, collectively implementing the computerized system 1 for determining efficacy of a medical treatment for a medical condition. Thus, although in the following description the implementation of the blockchains(s) and associated smart contracts is described with reference to the processors 11 of the computer system 10, one skilled in the art will understand that depending on the embodiment, the blockchains(s) and associated smart contracts are further implemented on processors of user computers 5 and/or member computers 6, for example, without deviating from the scope of the present application.

It should be pointed out that the processors of the computerized system 1, specifically the processors 11 of the computers of computer system 10, of the user computers 51, 52 and of the member computers 60, as well as the processors of the computers 30 of the data sources 3 and the data collection system 2 (including the secure UID platform 20) are controlled by computer program code (including smart contract code 82, 92) stored on non-transitory computer-readable medium, such as memory or storage disks, e.g. solid state drives (SSD). The program code is configured to control the respective processors such that the processors or their respective computers perform various functions, as described below with reference to FIGS. 2 and 3.

In the following paragraphs, an exemplary sequence of steps for determining the efficacy of a medical treatment for a medical condition are described with reference to FIG. 2.

In step S1, user data is received for setting up an assessment process for determining the efficacy of a medical treatment for a medical condition, particularly the efficacy of a medical drug or a medical device for treating the medical condition. The user data is entered by the provider and the contract authority on the respective user computers 51, 52. The user data is submitted by the user computers 5 via the communication network 7 to the computer system 10. For example, the user data is entered, negotiated and agreed upon by the provider and the contract authority via a web site or other software application implemented on one or more computers of the computer system 10. Specifically, the provider and the contract authority enter, negotiate and agree on the possible outcomes expected from the medical treatment of the medical condition, the population of patients 4 to be treated, and one or more data sources 3 for providing health care data related to the medical treatment of the targeted population of patients 4 for the medical condition, and the assessment periodicity or length of an assessment period, respectively, for example monthly, quarterly or semi-annually. For example, the targeted population of patients 4 to be treated is defined at a later point (after contract negotiation), whereby the individual patients are registered for the contracted medical treatment and assessment process. Each of the possible outcomes is assigned a rating level, indicative of how well or badly the medical treatment of the medical condition is considered to have worked at the realized outcome. For example, the rating levels cover a range from a worst case rating, indicative of no effect or even a negative effect, to a best case rating, indicative of an expected outcome achieved or even exceeded. In an embodiment, the outcome is represented by an outcome value, e.g. a number or a binary measure, which is compared to one or more rating threshold levels, indicative of a different reimbursement value (price) for the achieved outcome of the medical treatment. The definition of the medical treatment includes a specific medical drug and/or a medical device. Accordingly, the possible outcomes relate to expected and/or possible, desired and/or undesired results and effects from the use of the specific medical drug or medical device on the population of patients 4 targeted for the medical treatment of the medical condition. In an embodiment, the users further specify and agree on an aggregation level for the population of patients. The aggregation level includes age, sex, geographic region, and/or body mass index. In an embodiment, the aggregation level further includes disease characteristics.

In the embodiment and/or scenario where reference data from a reference population 6 is to be considered in the assessment of the efficacy of the medical treatment for the medical condition, the user data for setting up the assessment process further includes a definition or indication of the reference data and the reference population 6. Specifically, the provider and the contract authority enter, negotiate and agree on the fact that reference data is to be considered and, if that is the case, on the indication of the health care data to be collected as reference data and the type, definition, and/or specific indication of members of the reference population 6.

In step S2, the assessment smart contract 81 is generated and stored on the assessment blockchain 8. The processors 11 of the computer system 10 generate and store the smart contract 81, including its smart contract code 82 and assessment data structure 83. The assessment data structure 83 defines for the data collection system 2 the medical and health data (data records and data elements) which relate to the specified medical treatment of the specified population of patients 4 for the specified medical condition and are to be collected from the specified data sources 3 with the defined assessment periodicity. Particularly, the assessment data structure defines the medical and health data to be collected which relate to the specified outcomes from the medical treatment of the medical condition. More specifically, the assessment data structure defines the medical and health data to be collected which relate to the specified expected and/or possible, desired and/or undesired results and effects from the use of the specific medical drug or medical device used for the medical treatment of the medical condition. The assessment data structure 83 further defines an assessment block 84 to be generated and stored on the assessment blockchain 8 by the data collection system 2 for an assessment period, using the data records and data elements collected during the assessment period. The assessment block 84 indicates for the assessment period the outcomes actually achieved for the specified population of patients 4 by the medical treatment of the medical condition. The smart contract code 82 is configured to control the processors 11 of the computer system 10, such that the processors 11 determine the efficacy of the medical treatment for the medical condition for a particular assessment period, upon an assessment block 84 being stored by the data collection system 2 on the assessment blockchain 8 for the particular assessment period, using the outcomes indicated in the assessment block 84 for the population of patients 4 by the medical treatment of the medical condition with regards to the rating levels specified for the different possible outcomes. In terms of security and authenticity, the assessment smart contract 81 ensures that assessment blocks 84 are submitted by an authorized and authentic data collection system 2, e.g. by way of a cryptographically verifiable electronic certificate or signature, generated by the data collection system 2 using a secrete cryptographic key.

In the embodiment and/or scenario where the negotiated assessment of the efficacy of the medical treatment for the medical condition involves the collection and consideration of reference data from a reference population 6, the smart contract code 82 is further configured to control the processors 11 of the computer system 10, such that the processors 11 determine the efficacy of the medical treatment for the medical condition by further using the reference blocks 94, e.g. the reference data reported in the reference blocks 94, submitted by the respective members of the relevant reference population 6.

The assessment data structure 83 further defines for the data collection system 2 the specified aggregation level at which the data records and data elements are to be collected from the data sources 3, and at which the assessment block 84 is to indicate the outcomes actually achieved by the medical treatment of the medical condition. For generating the assessment data structure 83, defining the data records and the data elements, as well as the assessment block 84, coding standards are used, such as HL7 (Health Level 7, a standard for the data exchange of health data) and LOINC (Logical Observation Identifiers Names and Codes), a standard common language (identifiers, names, codes) for identifying health measurements, observations and documents, and ICD codes (International Statistical Classification of Diseases and Related Health Problems) for standardizing the coding of diseases, signs and symptoms, abnormal findings, complaints, social circumstances, and external causes of injury or diseases.

In the embodiment and/or scenario where the negotiated assessment of the efficacy of the medical treatment for the medical condition involves the collection and consideration of reference data from a reference population 6, a temporary blockchain 9 is generated for each of the members of the reference population 6, including a reference smart contract 91 with smart contract code 92 and a reference data structure 93. The processors 11 of the computer system 10 generate the temporary blockchains 9 and reference smart contracts 91 and store the reference smart contracts 91 for a particular member of the reference population 6 on the temporary blockchains 9 for the respective member of the reference population 6. The smart contract code 92 is configured to control the processors 11 of the computer system 10, such that the processors 11 transfer the reference block 94 to the assessment blockchain 8 for consideration in a particular assessment period. One skilled in the art will understand that in an alternative embodiment, the assessment smart contract 81 will retrieve the reference blocks 94 from the temporary blockchains 9 associated with the members of the reference population 6 to be considered in the assessment of the efficacy of the medical treatment for the medical condition for a particular assessment period. In terms of security and authenticity, the reference smart contract 91 ensures that reference blocks 94 are submitted by the authorized and authentic member of the reference population 6, e.g. by way of a cryptographically verifiable electronic certificate or signature, generated by the respective member computer 60 using a secrete cryptographic key of the respective member.

In step S3, the process for collecting medical and health data related to the medical treatment of the medical condition for the targeted population of patients 4 is setup and initiated. The data collection system 2 collects from the specified data sources 3 the medical and health data specified in the assessment data structure 83 for the defined assessment period and targeted population of patients 4. The data collection system retrieves and collects the medical and health data such as to enable a reporting and analysis on the aggregation levels specified by the smart contract 82 or its assessment data structure 83, respectively, per age (group), sex, geographic region, and/or body mass index. Depending on the implementation and/or configuration, the data collection system 2 is triggered by the smart contract 81 or another software program running on the computer system 10. For defining and executing the data collection process, the data collection system 2 obtains the assessment data structure 83 from the respective assessment smart contract 81 on the assessment blockchain 8, e.g. through active retrieval by the data collection system 2 or passively, as transferred by the assessment smart contract 81 or another software program running on the computer system 10.

In an embodiment, the data collection system 2 is further configured to collect the required medical and health data related to the medical treatment of the medical condition directly from individual members of the targeted population of patients 4, e.g. through an Internet-based software application and/or a software program, e.g. an app, installed and executing on a mobile or stationary communication terminal of the respective patient, e.g. a personal computer, a laptop, a mobile phone, a smart watch, or a tablet computer.

In step S4, at the end of an assessment period, an assessment block 84 is generated and stored on the assessment blockchain 8. The data collection system 2 generates the assessment block 84 as defined by the smart contract 82 or its assessment data structure 83, respectively. The assessment block 84 is generated using the medical and health data collected by the data collection system 2 from the data sources 3 for the assessment period. The assessment block 84 is generated to indicate the actually achieved outcomes related to the expected and/or possible, desired and/or undesired results and effects from the use of the specific medical drug or medical device on the population of patients 4 targeted for the medical treatment of the medical condition. The assessment block 84 is generated to reflect the aggregation levels specified by the smart contract 82 or its assessment data structure 83, respectively, per age (group), sex, geographic region, and/or body mass index. The assessment block 84 is stored on the assessment blockchain 8 related to the respective medical treatment of the medical condition and according to the protocol and algorithms of the blockchain platform underlying the assessment blockchain 8, e.g. Hyperledger, Ethereum, etc.

In the embodiment and/or scenario where the negotiated assessment of the efficacy of the medical treatment for the medical condition involves the collection and consideration of reference data from a reference population 6, the computers 60 of the respective members of the reference population 6 generate and store on the temporary blockchain 9, associated with the respective member, a reference block 94, as defined by the reference data structure 93, using the health care data provided by the member for the respective assessment period. The reference block 94 is stored on the reference blockchain 9 of the respective member of the reference population 6 according to the protocol and algorithms of the blockchain platform underlying the reference blockchain 9, e.g. Hyperledger, Ethereum, etc.

In step S5, upon storage of a new assessment block 84 on the assessment blockchain 8, the efficacy of the medical treatment is determined for the respective assessment period based on the new assessment block 84. Depending on the embodiment, configuration, and/or negotiated contractual agreement, the assessment block 84 indicates the achieved outcomes for the aggregation levels specified by the smart contract 82 or its assessment data structure 83, respectively, per age (group), sex, geographic region, and/or body mass index. The efficacy of the medical treatment is determined by rating the outcomes indicated in the assessment block 84, using the rating levels initially specified for the different possible outcomes. Specifically, the assessment smart contract 81 or its smart contract code 82, respectively, determines for the outcomes of the medical treatment for the medical condition, as indicated in the assessment block 84 for the respective assessment period, the corresponding rating levels specified for the different possible outcomes. The rating level of one outcome or the rating levels of a plurality of outcomes reported in the assessment block 84 define the efficacy of the medical treatment. If several outcomes are defined, the efficacy is calculated as a weighted average of the respective rating levels, whereby the weighting factors would also be part of the initial negotiation and agreement between the provider and the contract authority. In the embodiment and/or scenario where the negotiated assessment of the efficacy of the medical treatment for the medical condition involves the consideration of reference data from a reference population 6, the assessment smart contract 81 or its smart contract code 82, respectively, further include in the assessment the reference blocks 94 submitted by the respective members of the reference population 6 for the assessment period.

In step S6, based on the determined efficacy for the medical treatment, a transaction and/or a message is/are generated. In an embodiment, the data transaction, is generated between the contract authority and the provider of the medical treatment, depending on the efficacy, upon an assessment block being stored on the assessment blockchain for the particular assessment period. Accordingly, the contract authority as the payer reimburses the provider of medical treatment depending on the determined efficacy of the treatment. Alternatively or in addition, the determined level of efficacy is reported in a message, e.g. to the contract authority, the provider of medical treatment, and/or other recipient as previously specified the initial negotiation and agreement between the provider and the contract authority.

Figure 2:
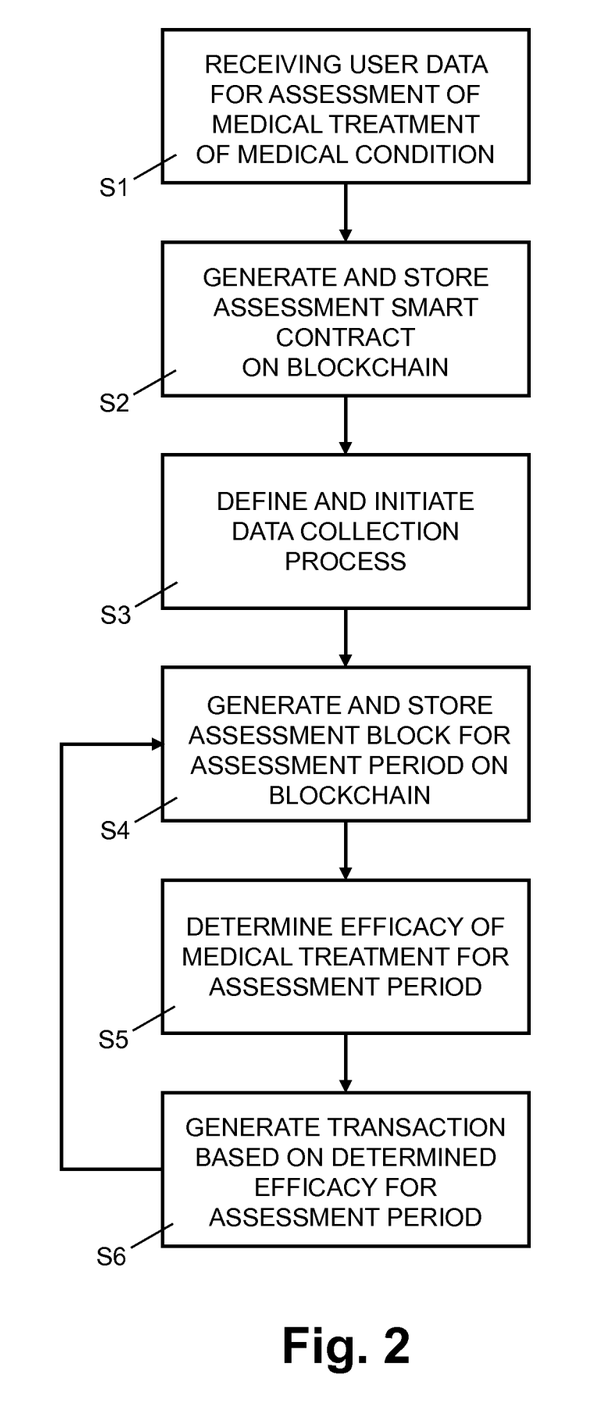
FIG. 2: shows a flow diagram illustrating schematically an exemplary sequence of steps for determining efficacy of a medical treatment for a medical condition.

As illustrated in FIG. 2, subsequently, processing continues in step S4 by the data collection system 2 generating the assessment block 84 for the next assessment period, using the medical and health data related to the targeted population of patients 4 as collected by the data collection system 2 for the subsequent assessment period, and storing the assessment block 84 on the assessment blockchain 8, as described above.

Table 1 shown below, summarizes process steps performed, e.g. by the computer system 10, for determining efficacy of a medical treatment for a medical condition with reference to FIG. 3. The label "REIMBURSE" relates to the computer system 10. The label "INSIGHTS" relates to the data lake implemented by the data collection system 2. In Table 1, API refers to Application Programming Interface. "DIGIPHARM permissioned Blockchain" refers to the assessment blockchain 8. "REIMBURSE Smart Contract"

refers to the assessment smart contract 81 on the assessment blockchain 8. HCP refers to Health Care Provider.

a smart contract is defined and generated as described above in the context of step S2. As indicated in Table 1 by process

TABLE 1

| Process Step | Description | Integration | Actor | Architecture related object |
|---|---|---|---|---|
| A | Contract negotiations | WebApp | Provider Contract Authority | Off-line/off-chain |
| B | Creation of contract | WebApp to API (Smart Contract definition) | Computer System | SmartContract |
| B.1 | Validation API call | To LOINC.org for outcome codes. | Computer System | REIMBURSE - SmartContract |
| B.2 | Validation API call | To HL7.org for Outcome measure field structure | Computer System | REIMBURSE - SmartContract |
| C | Submission API call | To DIGIPHARM permissioned blockchain | Computer System | REIMBURSE - SmartContract |
| C.1 | Contract approved | WebApp to API (SmartContract creation and distribution to Blockchain relevant channels and nodes) | Contract Authority | REIMBURSE - SmartContract |
| C.2 | Contract distribution of relevant contract segments to the Data Lake for Outcomes calculation | Blockchain channel/node for Data collection system/Data Lake | Computer System | REIMBURSE - Data Lake integration node |
| D | Registered patients and/or relevant for contract share associated health records for relevant outcomes | Data collection system/Data lake ingests/consumes relevant records | Computer System | INSIGHTS - Data lake ingestion/consumption procedures |
| D.1 | Association to smart contract | To the Smart Contract over the Blockchain | Computer System | REIMBURSE - Integration with Data Lake |
| E | Patient onboarding/Identification | To source systems or individuals to identify relevant Health records | HCP and Patients | Local HCP systems or centralized registry |
| F | Data anonymization | Data lake anonymization services prepare data for consumption | Computer System | INSIGHTS - Data lake ingestion/consumption procedures |
| G | Data cleansing, mapping and curating is performed | Data lake integration services | Computer System | INSIGHTS - Data lake ingestion/consumption procedures |
| H | API integration | To the REIMBURSE blockchain based on outcome aggregation and periodicity | Computer System | INSIGHTS - Integration to REIMBURSE |

Figure 3:
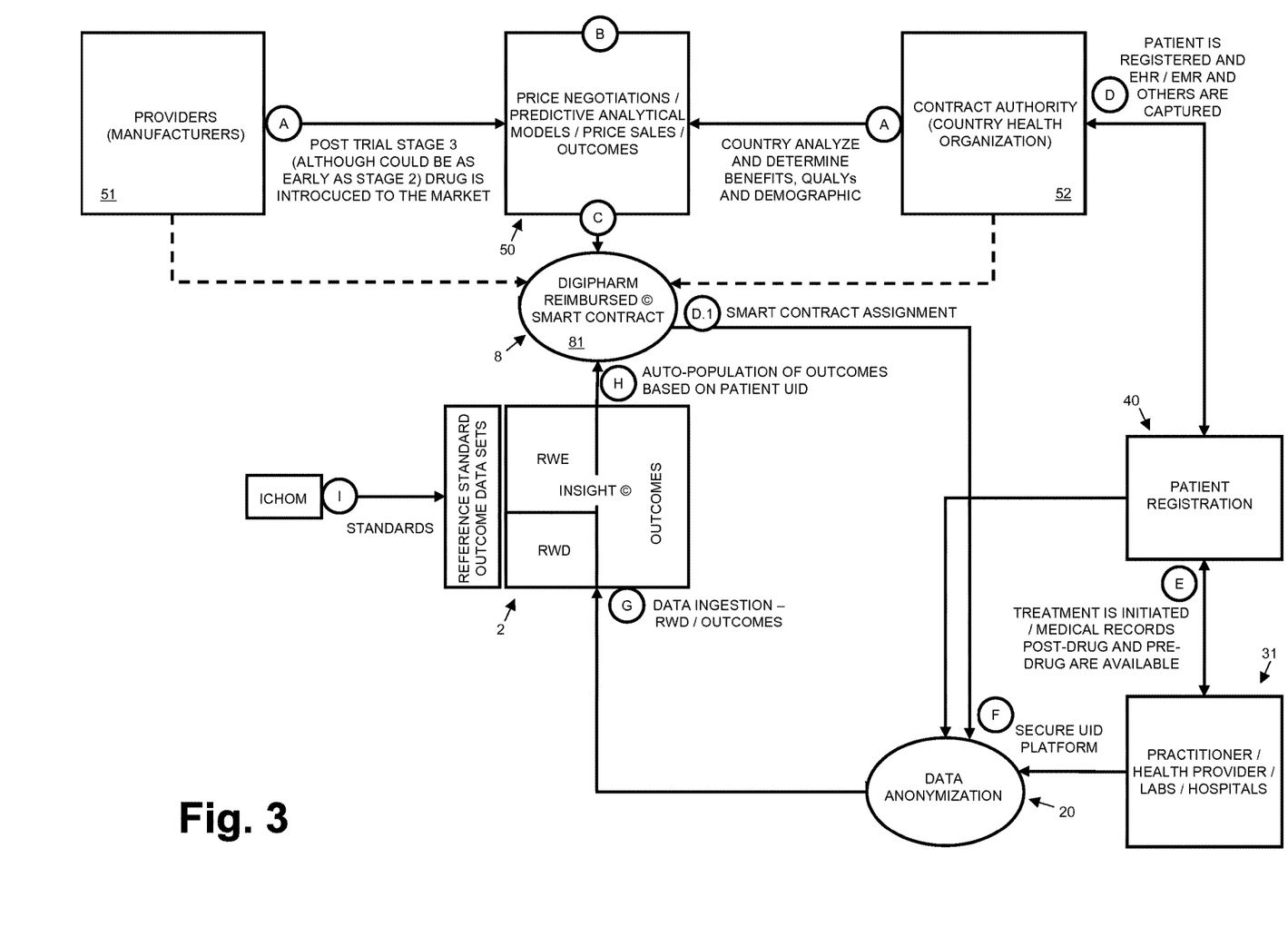
FIG. 3: shows a block diagram illustrating schematically a computer system and an exemplary sequence of steps for determining efficacy of a medical treatment for a medical condition.

In FIG. 3, RWE refers to "Real World Evidence" and RWD refers to "Real World Data" collected by the data collection system 2 as medical and health care data from various data sources 3 in order to generate the outcomes required for assessing the efficacy of a medical treatment for a medical condition. ICHOM refers to the International Consortium for Health Outcomes Measurement which defines and provides standard sets for measurements of patient related outcomes. EHR refers to Electronic Health Record and EMR refers to Electronic Medical Record, which define and constitute electronically-stored health information in a digital format for a patient.

As indicated in Table 1 and illustrated in FIG. 3, in process step A, a contract is negotiated and agreed upon between a provider 1, e.g. a manufacturer of a medical drug or medical device for medical treatment of a medical condition, and a contract authority 52, e.g. a national health care organization or health care provider, as described above in the context of step S1. Parts of the negotiations may be conducted off-line/off-chain; other parts of the negotiations are executed in a computerized fashion through on-line negotiations, e.g. via an Internet-based application, as described above in the context of step S1. Typically, the assessment of the efficacy of the medical treatment or the relevant drug or medical device is initiated at post trial stage 3 (it could be initiated as early as stage 2) when the drug or device is introduced to the market by the provider 51. The contract authority 52 will conduct analysis of and determines benefits, qualification criteria, and relevant demographics, etc.

In process step B, based on the negotiated contract data 50, resulting from various contractual parameters such as price, predictive analytical models, and expected outcomes, steps B.1, B.2, generating the contract data 50 and the related smart contact makes use of coding standards for outcome codes and data (field) structures for outcome measures, specifically, HL7 (Health Level 7) and LOINC (Logical Observation Identifiers Names and Codes), as introduced above in the context of step S2.

In process step C, the generated smart contract is stored as assessment smart contract 81 on the assessment blockchain 8, as described above in the context of step S2. As indicated in Table 1 by process step C.1, this includes distributing the approved smart contract to the blockchain relevant channels and nodes. Furthermore, as indicated by process step C.2 in Table 1, the data collection system 2 is informed about the medical and health data to be collected and the outcomes to be generated and reported, as described above in the context of step S3.

In process step D, the population of patients 4 which are to be treated for the respective medical condition and are to be included in the assessment process are registered and their respective HER/MHR (Electronic Health Record/Electronic Medical Record) are captured, as indicated by patient registration 40. Specifically, individual patients to be included in the targeted population of patients 4 are registered for the contracted medical treatment and assessment process, e.g. linked to an identifier of the contract or medical treatment and assessment program.

In process step D.1, the assessment smart contract 81 is assigned to the registered population of patients 4. For example, the assessment smart contract 81 is registered with the data collection system 2; specifically, the assessment smart contract 81 registers an identifier of the contract or medical treatment and assessment program with the secure UID platform 20 of the data collection system 2 for data anonymization of personal and confidential medical and health data of the registered population of patients 4 to be included in the assessment process.

In process step E, medical treatment of the medical condition is initiated for the registered population of patients 4 and their medical records (pre-treatment status and post-treatment status) are made available by the practitioners, health providers, labs, and/or hospitals 31.

In process step F, the secure UID platform 20 of the data collection system 2 implements data anonymization of the medical and health data of the registered population of patients 4 to be included in the assessment process, by retrieving and collecting from the data sources 3 the medical and health data for the population of patients 4 registered for the contracted medical treatment, without using any personal patient identification information but an assigned "anonymous" User Identifier (UID).

In process step G, the anonymized medical and health data of the registered population of patients 4 is "ingested" as Real World Data (RWD) and Real World Evidence (RWE) to the data collection system 2. As indicated in FIG. 3, the data collection system 2 performs data cleansing, mapping and curating procedures for the collected medical and health data, before determining the actual outcomes achieved in the respective assessment period by the medical treatment of the medical condition of the registered population of patients 4, as described above in the context of step S4.

In process step H, the outcomes for the assessment period are reported automatically by the data collection system 2 in assessment blocks 84 onto the assessment blockchain 8, as described above in the context of step S4. The data collection system 2 generates and stores on the assessment blockchain 8 an assessment block 84 with the outcomes achieved by the medical treatment of the medical condition of the registered population of patients, by the overall group of the registered population of patients 4 or by individual patients identified by their anonymized UID.

As illustrated schematically in FIG. 3 by process step I, the data collection system 2 makes use of ICHOM (International Consortium for Health Outcomes Measurement) standard sets for measurements of patient related outcomes.

It should be noted that, in the description, the computer program code has been associated with specific functional modules and the sequence of the steps has been presented in a specific order, one skilled in the art will understand, however, that the computer program code may be structured differently and that the order of at least some of the steps could be altered, without deviating from the scope of the invention.

The invention claimed is:

1. A computer system for determining efficacy of a medical treatment for a medical condition, the system comprising one or more processors configured to perform the steps of:
   receiving from one or more users, prior to performing the medical treatment of the medical condition:
   i) indications of a plurality of possible outcomes expected from the medical treatment of the medical condition,
   ii) identification of a population of patients to be treated,
   iii) identification of one or more data sources for providing health care data related to the medical treatment of the population for the medical condition, and
   iv) a definition of an assessment periodicity;
   generating and storing on an assessment blockchain, related to collecting and processing health care data for determining the efficacy of the medical treatment for the medical condition:
   i) an assessment smart contract, the assessment smart contract comprising smart contract code and an assessment data structure, the assessment data structure defining for a data collection system data records and data elements which relate to the medical treatment of the population for the medical condition and are to be collected from the data sources with the defined assessment periodicity, and
   ii) an assessment block to be generated and stored on the assessment blockchain by the data collection system for an assessment period, as defined by the assessment periodicity, using the data records and data elements collected during the assessment period,
   the assessment block indicating for the assessment period the outcomes actually achieved for the population by the medical treatment of the medical condition,
   the smart contract code being configured to control the one or more processors, such that the processors determine the efficacy of the medical treatment for the medical condition for a particular assessment period, upon an assessment block being stored by the data collection system on the assessment blockchain for the particular assessment period, using the outcomes indicated in the assessment block for the population by the medical treatment of the medical condition;
   receiving from the one or more users indications of a reference population;
   generating temporary blockchains for members of the reference population; and
   generating on each of the temporary blockchains a references smart contract related to the respective member of the reference population, the references smart contract comprising:
   i) smart contract code, and
   ii) a reference data structure,
   the reference data structure defining data records and data elements which relate to reference data from the respective member of the reference population to be considered in determining the efficacy of the medical treatment for the medical condition,
   the smart contract code of the references smart contract being configured to control the one or more processors to generate and store on the temporary blockchain and/or on the assessment blockchain a reference block; and
   the smart contract code of the assessment smart contract being configured to control the one or more processors, such that the processors use the reference block in determining the efficacy of the medical treatment for the medical condition.

2. The computer system of claim 1, wherein the processors are further configured to receive from the one or more users a rating level for each of the expected outcomes; and to generate smart contract code configured to control the one or more processors, such that the processors determine the efficacy of the medical treatment by rating the outcomes indicated in the assessment block, using the rating levels indicated for the expected outcomes, upon an assessment block being stored on the assessment blockchain for the particular assessment period.

3. The computer system of claim 1, wherein the processors are further configured to receive from the one or more users an aggregation level for the population of patients, the aggregation level including at least one of: age, sex, geographic region, and body mass index; and to generate the assessment data structure to further define for the data collection system the aggregation level at which the data records and data elements are to be collected from the data sources, and at which the assessment block is to indicate the outcomes actually achieved by the medical treatment of the medical condition.

4. The computer system of claim 1, wherein the processors are further configured to receive from the one or more users an indication of at least one of: a medical device and a medical drug, to be used in the medical treatment of the medical condition; to generate the assessment data structure configured to define for the data collection system data records and data elements which relate to the use of the medical device or medical drug, respectively, in the treatment of the medical condition, and to define the assessment block to indicate the outcomes actually achieved by the use of the medical device or medical drug, respectively, in the treatment of the medical condition; and to generate smart contract code configured to control the one or more processors, such that the processors determine the efficacy of the medical device or medical drug, respectively, for the treatment of the medical condition, using the outcomes indicated in the assessment block for using the medical device or medical drug, respectively, in treatment of the medical condition.

5. The computer system of claim 1, wherein the processors are further configured to generate smart contract code configured to control the one or more processors, such that the processors generate a data message, depending on the efficacy, upon an assessment block being stored on the assessment blockchain for the particular assessment period.

6. The computer system of claim 1, wherein the processors are further configured to receive from the one or more users indications of a provider of the medical treatment and a contract authority; and to generate smart contract code configured to control the one or more processors, such that the processors generate a data transaction, between the contract authority and the provider of the medical treatment, depending on the efficacy, upon an assessment block being stored on the assessment blockchain for the particular assessment period.

7. The computer system of claim 1, wherein the processors are further configured to use one or more defined coding standards for generating the assessment data structure to define for the data collection system the data records and data elements, and the assessment block.

8. A computer-implemented method for determining efficacy of a medical treatment for a medical condition, the method comprising one or more processors performing the steps of:
receiving from one or more users, prior to performing the medical treatment of the medical condition:
i) indications of a plurality of possible outcomes expected from the medical treatment of the medical condition,
ii) identification of a population of patients to be treated,
iii) identification of one or more data sources for providing health care data related to the medical treatment of the population for the medical condition, and
iv) a definition of an assessment periodicity;

generating and storing on an assessment blockchain, related to collecting and processing health care data for determining the efficacy of the medical treatment for the medical condition:
i) an assessment smart contract, the assessment smart contract comprising smart contract code and an assessment data structure, the assessment data structure defining for a data collection system data records and data elements which relate to the medical treatment of the population for the medical condition and are to be collected from the data sources with the defined assessment periodicity, and
ii) an assessment block to be generated and stored on the assessment blockchain by the data collection system for an assessment period, as defined by the assessment periodicity, using the data records and data elements collected during the assessment period, the assessment block indicating for the assessment period the outcomes actually achieved for the population by the medical treatment of the medical condition, and
the smart contract code being configured to control the one or more processors, such that the processors determine the efficacy of the medical treatment for the medical condition for a particular assessment period, upon an assessment block being stored by the data collection system on the assessment blockchain for the particular assessment period, using the outcomes indicated in the assessment block for the population by the medical treatment of the medical condition;
receiving from the one or more users indications of a reference population;
generating temporary blockchains for members of the reference population; and
generating on each of the temporary blockchains a references smart contract related to the respective member of the reference population, the references smart contract comprising:
i) smart contract code, and
ii) a reference data structure,
the reference data structure defining data records and data elements which relate to reference data from the respective member of the reference population to be considered in determining the efficacy of the medical treatment for the medical condition,
the smart contract code of the references smart contract being configured to control the one or more processors to generate and store on the temporary blockchain and/or on the assessment blockchain a reference block, and
the smart contract code of the assessment smart contract being configured to control the one or more processors, such that the processors use the reference block in determining the efficacy of the medical treatment for the medical condition.

9. The method of claim 8, further comprising the processors receiving from the one or more users a rating level for each of the expected outcomes; and generating smart contract code configured to control the one or more processors, such that the processors determine the efficacy of the medical treatment by rating the outcomes indicated in the assessment block, using the rating levels indicated for the expected outcomes, upon an assessment block being stored on the assessment blockchain for the particular assessment period.

10. The method of claim 8, further comprising the processors receiving from the one or more users an aggregation level for the population of patients, the aggregation level including at least one of: age, sex, geographic region, and body mass index; and generating the assessment data structure to further define for the data collection system the aggregation level at which the data records and data elements are to be collected from the data sources, and at which the assessment block is to indicate the outcomes actually achieved by the medical treatment of the medical condition.

11. The method of claim 8, further comprising the processors receiving from the one or more users an indication of at least one of: a medical device and a medical drug, to be used in the medical treatment of the medical condition; generating the assessment data structure configured to define for the data collection system data records and data elements which relate to the use of the medical device or medical drug, respectively, in the treatment of the medical condition, and to define the assessment block to indicate the outcomes actually achieved by the use of the medical device or medical drug, respectively, in the treatment of the medical condition; and generating smart contract code configured to control the one or more processors, such that the processors determine the efficacy of the medical device or medical drug, respectively, for the treatment of the medical condition, using the outcomes indicated in the assessment block for using the medical device or medical drug, respectively, in treatment of the medical condition.

12. The method of claim 8, further comprising the processors generating smart contract code configured to control the one or more processors, such that the processors generate a data message, depending on the efficacy, upon an assessment block being stored on the assessment blockchain for the particular assessment period.

13. The method of claim 8, further comprising the processors (11) receiving from the one or more users indications of a provider of the medical treatment and a contract authority; and generating smart contract code configured to control the one or more processors, such that the processors generate a data transaction, between the contract authority and the provider of the medical treatment, depending on the efficacy, upon an assessment block being stored on the assessment blockchain for the particular assessment period.

14. The method of claim 8, further comprising the processors using one or more defined coding standards for generating the assessment data structure to define for the data collection system the data records and data elements, and the assessment block.

15. A computer program product comprising a non-transitory computer-readable medium having stored thereon computer program code configured to control one or more processors of a computer system, such that the computer system performs the steps of:
  receiving from one or more users, prior to performing a medical treatment of a medical condition,
    i) indications of a plurality of possible outcomes expected from the medical treatment of the medical condition,
    ii) identification of a population of patients to be treated,
    iii) identification of one or more data sources for providing health care data related to the medical treatment of the population for the medical condition, and
    iv) a definition of an assessment periodicity;
  generating and storing on an assessment blockchain, related to collecting and processing health care data for determining the efficacy of the medical treatment for the medical condition:
    i) an assessment smart contract, the assessment smart contract comprising smart contract code and an assessment data structure, the assessment data structure defining for a data collection system data records and data elements which relate to the medical treatment of the population for the medical condition and are to be collected from the data sources with the defined assessment periodicity, and
    ii) an assessment block to be generated and stored on the assessment blockchain by the data collection system for an assessment period, as defined by the assessment periodicity, using the data records and data elements collected during the assessment period,
  the assessment block indicating for the assessment period the outcomes actually achieved for the population by the medical treatment of the medical condition, and
  the smart contract code being configured to control the one or more processors, such that the processors determine the efficacy of the medical treatment for the medical condition for a particular assessment period, upon an assessment block being stored by the data collection system on the assessment blockchain for the particular assessment period, using the outcomes indicated in the assessment block for the population by the medical treatment of the medical condition;
  receiving from the one or more users indications of a reference population;
  generating temporary blockchains for members of the reference population; and
  generating on each of the temporary blockchains a references smart contract related to the respective member of the reference population, the references smart contract comprising:
    i) smart contract code, and
    ii) a reference data structure,
  the reference data structure defining data records and data elements which relate to reference data from the respective member of the reference population to be considered in determining the efficacy of the medical treatment for the medical condition,
  the smart contract code of the references smart contract being configured to control the one or more processors to generate and store on the temporary blockchain and/or on the assessment blockchain a reference block, and
  the smart contract code of the assessment smart contract being configured to control the one or more processors, such that the processors use the reference block in determining the efficacy of the medical treatment for the medical condition.

* * * * *